United States Patent
Olivas et al.

(10) Patent No.: US 6,784,344 B2
(45) Date of Patent: Aug. 31, 2004

(54) PACER LETTUCE VARIETY

(75) Inventors: Nathan K. Olivas, Salinas, CA (US); Nathan J. Olivas, Salinas, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 10/052,061

(22) Filed: Jan. 16, 2002

(65) Prior Publication Data

US 2002/0166148 A1 Nov. 7, 2002

Related U.S. Application Data

(60) Provisional application No. 60/262,308, filed on Jan. 17, 2001.

(51) Int. Cl.[7] .............................. A01H 4/00; A01H 5/00; A01H 5/10

(52) U.S. Cl. ....................... 800/305; 435/410; 800/260; 800/298

(58) Field of Search .......................... 435/410; 800/260, 800/298, 305

(56) References Cited

PUBLICATIONS

De Vries et al 1994, Plant Systematics and Evolution 193: 125–141.*
Ryder et al 1994, HortScience 33(5): 903–904.*

* cited by examiner

*Primary Examiner*—David H Kruse
(74) *Attorney, Agent, or Firm*—Morrison & Foerster LLP

(57) ABSTRACT

A new lettuce variety designated Pacer is described. Pacer is an iceberg lettuce variety exhibiting stability and uniformity. Pacer lettuce seed are deposited with the American Type Culture Collection and have ATCC deposit number PTA-4010.

8 Claims, 1 Drawing Sheet

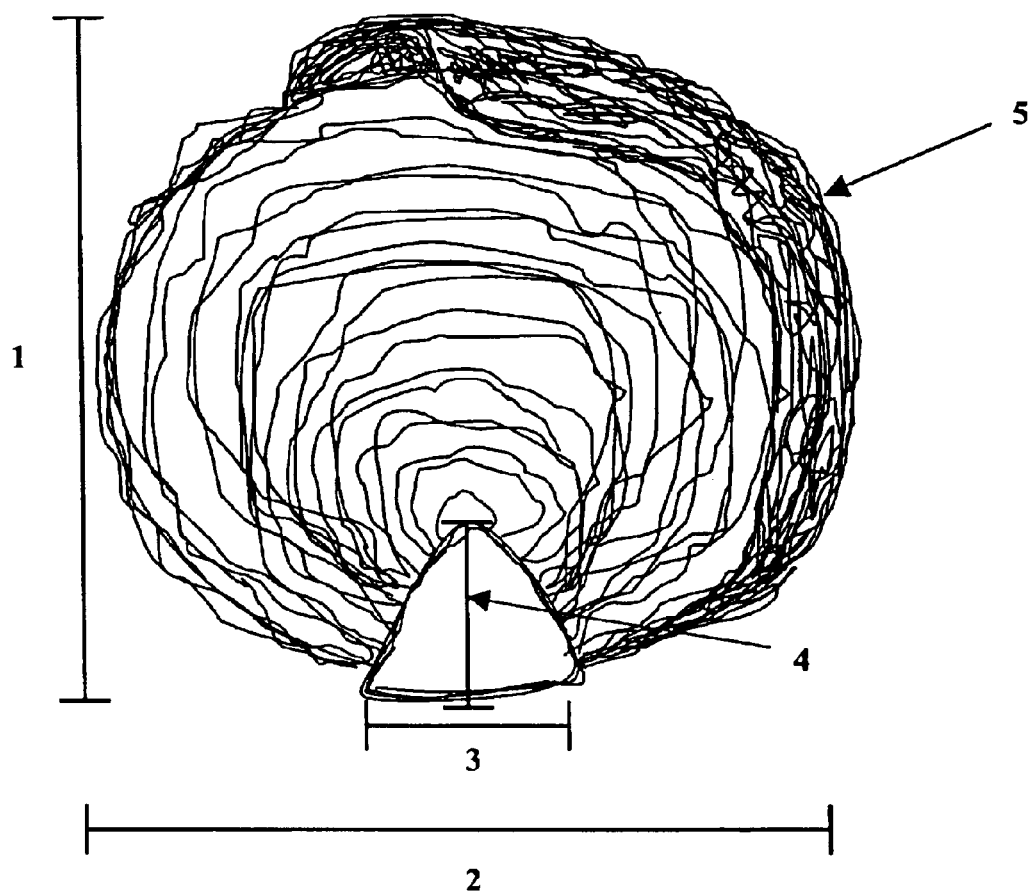
FIGURE 1: Sliced Iceberg Lettuce

PACER LETTUCE VARIETY

I. RELATED APPLICATION

This application claims the benefit under 35 U.S.C. § 119(e) of U.S. provisional patent application No. 60/262,308, filed Jan. 17, 2001, which is hereby incorporated by reference in its entirety.

II. FIELD OF THE INVENTION

This invention relates to the field of plant breeding. In particular, this invention relates to a new lettuce, *Lactuca sativa*, variety, Pacer.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

IV. SUMMARY OF THE INVENTION

In order to meet these needs, the present invention is directed to an improved iceberg lettuce variety that exhibits vigorous growth, increased weight and yield. In particular, the present invention is directed to lettuce, *Lactuca sativa*, seed designated as Pacer having ATCC Accession Number PTA-4010. The present invention is further directed to a lettuce, *Lactuca sativa* plant produced by growing Pacer lettuce seed having ATCC Accession Number PTA-4010. The present invention is further directed to a *Lactuca sativa* plant having all the physiological and morphological characteristics of a *Lactuca sativa* plant produced by growing Pacer lettuce seed having ATCC Accession Number PTA-4010. The present invention is further directed to a $F_1$ hybrid lettuce, *Lactuca sativa* plant having Pacer as a parent wherein Pacer is grown from Pacer lettuce seed having ATCC Accession Number PTA-4010.

The present invention is further directed to pollen and ovules isolated from Pacer lettuce plants. The present invention is further directed to tissue culture of Pacer lettuce plants.

The present invention is further directed to a method of selecting lettuce plants comprising a) growing parental Pacer lettuce plants wherein the parental Pacer plants are grown from lettuce seed having ATCC Accession Number PTA-4010 and b) selecting a progeny plant from step a) wherein said progeny plant is phenotypically distinguishable from the Pacer plant. The present invention is further directed to lettuce plants and seeds produced by the lettuce plants wherein the lettuce plants are-isolated by the selection method of the invention.

The present invention is further directed to a method of breeding lettuce plants comprising crossing a lettuce plant with a plant grown from Pacer lettuce seed having ATCC Accession Number PTA-4010. The present invention is further directed to lettuce plants and seeds produced therefrom where the lettuce plant is isolated by the breeding method of the invention.

V. BRIEF DESCRIPTION OF THE DRAWING

The invention will be better understood by reference to FIG. 1 which shows a drawing of cross-section of an iceberg lettuce head showing: 1) head length, 2) head diameter, 3) core diameter, 4) core length, and a 5) wrapper leaf.

VI. BRIEF DESCRIPTION OF THE TABLE

The invention will be better understood by reference to the Table in which;

Table 1 shows trial data comparing Pacer and Desert Queen iceberg lettuce varieties.

VII. DETAILED DESCRIPTION OF THE INVENTION

In order to more clearly understand the invention, the following definitions are provided:

Iceberg Lettuce: Iceberg lettuce, *Lactuca sativa* L. var. capitala L. is also known as 'crisp head' lettuce. Iceberg lettuce is a lettuce plant type that forms a firm, spherical head formed with tightly folded brittle textured foliage as illustrated in FIG. 1. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Average Head Diameter: Average head diameter is an average of the measured head diameter and head length of the lettuce head.

Average Head Diameter: Core Length Ratio The ratio of the average head diameter to core length is indicative of the percentage of useable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage of maturity when a lettuce plant is ready for commercial lettuce harvest. In the case of an iceberg lettuce variety, a lettucehead is at market state when the head is solid and has reached an adequate size and weight.

Big Vein: Big Vein a viral disease known to infect lettuce as described in U.S. Pat. No. 5,684,226 which is hereby incorporated by reference. Resistance to big vein disease via infection through *Olpidiurn brassicae* refers to a level of resistance in a novel lettuce variety as measured by visual symptoms. Resistance is deemed present when symptoms are not present in at least 85% of the novel variety plants when compared to a known resistant lettuce variety growing under comparable conditions to the novel variety.

Taking into account these definitions, the present invention is directed to seeds of the lettuce variety Pacer, plants produced by growing Pacer lettuce seeds, one or more plants selected from a collection of Pacer plants and seeds derived or produced therefrom; plants produced by crossing a lettuce plant with a Pacer lettuce plant and seeds derived or produced therefrom.

VIII. Origin and Breeding History of the Variety Pacer

Pacer is an iceberg lettuce variety developed from a hand pollinated cross of PAG 02-23, and Desert Queen made in year 1 in the San Joaquin Valley, Calif. PAG 02-23 is a white seeded selection from the commercial variety Raider. Both Raider and Desert Queen are heat tolerant iceberg types of lettuce available from Genecorp Seeds. Desert Queen, an Empire type was selected for its size, tip burn and bolting resistance, and Raider a Vanguard type was selected for its heat tolerance, texture and type. The cross was made producing a heat resistant Vanguard type iceberg lettuce variety designed for the early fall plantings in Huron Calif., a slot that is typically dominated by Empire type varieties.

Approximately 40 plants of the F1 seed were planted in a San Joaquin Valley production field for increase in year 2. The block was rogued, eliminating the self pollinating plants. The F2 seed was harvested.

Forty plants from the F2 seed were grown out in year 3 in a San Joaquin Valley, Calif. research seed production field. Multiple individual plant selections were made at the market stage, selecting slow bolting Vanguard type plants with large head and frame. These plants were harvested individually producing the F3 seed in the fall.

The F3 seed lines were extensively trialed throughout the growing seasons in years 3 and 4 in Yuma, Ariz. and Huron, Calif. A selected line was increased in year 5 in a San Joaquin Valley, Calif. research production filed. Large heading, slow bolting Vanguard type plants were individually selected and harvested. The remainder of the block was intensely rogued for uniformity in type, size and maturity until harvest. These remaining plants were bulk harvested producing F4 trial seed in the fall of year 5. The F4 seed lines were evaluated in research and development plot trials in Huron Calif. during year 6, where further selections were made for type and performance. These selections were dug from the trial and grown to seed in our San Martin green house facility.

After demonstrating good uniformity and performance in the research plots, larger strip trials of the F4 trial seed were conducted in the year 7 growing season in Huron, Calif., where it demonstrated good uniformity and stability. Seed from a single F4 plant selection was increased in year 9 in a San Joaquin Valley, Calif. research production field and selectively rogued for uniformity of type, size and maturity. The variety was noted to demonstrate good uniformity, the desired vanguard type, and good heat resistance. The F5 seed was harvested in the fall of year 9.

The F5 seed demonstrated excellent uniformity and stability and was free of variants when evaluated in trials in the fall of year 10 in Huron Calif. This variety exhibited excellent heat resistance in terms of its slow bolting and tip burn resistance. In May of year 10, the F5 seed was increased in our San Joaquin Valley commercial seed production block. The variety was stable and uniform, and the F6 seed was harvested in early September.

Grow out trials of the F6 seed planted in late December of year 10 in Yuma Ariz. showed the variety to be true to type, uniform, stable, and free of variants. Pacer as evaluated in commercial trials and seed production has been uniform and stable for two generations.

As evaluated in seed production and field trials, the F5 and F6 seed from the variety Pacer has been uniform and stable with out variants.

*Lactuca sativa* cultivar Pacer has numerous distinguishing characteristics as outlined in the following list.

Variety Description Information

| | |
|---|---|
| Plant Type: | Iceberg |
| Seed: | |
| Seed Color: | White |
| Light Dormancy: | No |
| Heat Dormancy: | Yes |
| Cotyledons: | |
| Shape of Cotyledons: | Spatulate |
| Shape of Fourth Leaf: | Elongated/Spatulate |
| Length/Width Index of Fourth Leaf: | 20 |
| Apical Margin: | Finely Dentate |
| Basal Margin: | Moderately Dentate |
| Undulation: | Flat |
| Green Color: | Dark |
| Anthocyanin: | |
| Distribution: | None |
| Rolling: | Absent |
| Cupping: | Uncupped |
| Reflexing: | Lateral Margins |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Dark |
| Anthocyanin | |
| Distribution: | None |
| Size: | Medium |
| Glossiness: | Moderate |
| Blistering: | Moderate |
| Leaf Thickness: | Intermediate |
| Trichomes: | Absent |

Comparison to Parent Line

| Characteristic | Pacer | Desert Queen |
|---|---|---|
| Spread of Frame Leaves | 48 cm | 46 cm |
| Head Diameter (market trimmed with single cup leaf) | 16 cm | 17 cm |
| Head Shape | Spherical | Spherical |
| Head Size Class | Medium | Medium |
| Head Count per Carton | 24 | 24 |
| Head Weight | 756 g | 806 g |
| Head Firmness | Firm | Firm |
| Butt | Round | Flat |
| Shape | Round | Flat |
| Midrib | Moderately Raised | Flattened |
| Core (Stem of Market-trimmed Head) | | |
| Diameter at the base of the Head | 3.4 cm | 3.0 |
| Ratio of Head Diameter/Core Diameter | 4.7 | 5.66 |
| Core Height from base of Head to Apex | 4.7 cm | 4.2 cm |
| Number of Days from First Water Date to Seed Stalk Emergence (Summer condition) | 64 | 72 |
| Bolting Class | Slow | slow |
| Height of Mature Seed Stalk | 85 cm | 82 cm |

-continued

| Characteristic | Pacer | Desert Queen |
|---|---|---|
| Spread of Bolter Plant | 39 cm | 41 cm |
| Bolter Leaves | Curved | Curved |
| Margin | Dentate | Dentate |
| Color | Medium | Light |
| Bolter Habit | | |
| Terminal Inflorescence | Present | Absent |
| Lateral Shoots (above head) | Absent | Present |
| Basal Side Shoots | Absent | Absent |
| Adaptation Regions | Huron, California | Yuma, Arizona. Huron, California |

Growing Season

| Season | Pacer | Desert Queen |
|---|---|---|
| Spring area | | |
| Summer area | | |
| Fall area | Huron, California | Yuma, Arizona. Huron California |
| Greenhouse: Not tested | | |

Diseases and Stress Reactions

| Disease or Stress | Pacer | Desert Queen |
|---|---|---|
| Virus | | |
| Big Vein: | NA | |
| Lettuce Mosaic: | NA | |
| Cucumber Mosaic: | Not Tested | |
| Broad Bean Wilt: | Not Tested | |
| Turnip Mosaic: | Not Tested | |
| Best Western Yellows: | Not Tested | |
| Lettuce Infectious Yellows: | Not Tested | |

Fungi/Bacteria

| Fungal/Bacterial | Pacer | Desert Queen |
|---|---|---|
| Corky Root Rot (Pythium Root Rot): | Susceptible | Susceptible |
| Downy Mildew (Races I, IIA, III): | Not Tested | |
| Powdery Mildew: | Not Tested | |
| Sclerotinia Rot: | Not Tested | |
| Bacterial Soft Rot (Pseudomonas spp. & others): Not tested | Not Tested | |
| Botrytis (Gray Mold): | Not Tested | |
| Other: Corky Root Rot (*Rhizomonas suberifaciens*): | Susceptible | Susceptible |

Insects

| Insects | Pacer | Desert Queen |
|---|---|---|
| Cabbage Loopers: | Not Tested | |
| Root Aphids: | Not Tested | |
| Green Peach Aphid: | Not Tested | |

Physiological/Stress

| Stress | Pacer | Desert Queen |
|---|---|---|
| Tipburn | Tolerant | Tolerant |
| Heat | Tolerant | Tolerant |
| Drought | Not Tested | |
| Cold | Not Tested | |

Post Harvest

| Characteristic | Pacer | Desert Queen |
|---|---|---|
| Pink Rib | Tolerant | |
| Russet Spotting | Not Tested | |
| Rusty Brown Discoloration | Not Tested | |
| Internal Rib Necrosis (Blackheart, Gray Rib, Gray Streak) | Not Tested | |
| Brown Stain | Not Tested | |

The present invention is further directed to the use of Pacer lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color and texture of the lettuce head. Crosses are made, for example, to produce a dark green, sure heading iceberg lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10–20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60–90 min past sunrise, flowers to be used for crossings are selected. The basis for selection are open flowers, with the stigma emerged and the pollen visibly attached to the single stigma (about 10–20 stigma). Using 3–4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2–3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907–908 both of which are hereby incorporated by reference in their entirety.

B. Selection

In addition to crossing, selection may be used to isolate lettuce new lettuce lines. In lettuce selection, one or more lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determined if they exhibit the desired characteristics of the originally selected line. Selection work is continued over multiple generations to increase the uniformity of the new line.

IX. Deposit Information

Applicants have made available to the public without restriction a deposit of at least 2500 seeds of lettuce variety Pacer with the American Type Culture Collection (ATCC), P.O. BOX 1549, MANASSAS, Va. 20108 USA, with a deposit on Jan. 24, 2002 which has been assigned ATCC number PTA-4010.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

X. EXAMPLES

Example 1

General Trialing Method

I. Set Up

The following steps illustrate the general trialing method of the invention.

1. A trial is set up to compare one or more lines. Parental lines and competing varieties are identified.

2. Primary slots are identified.

3. Necessary accession lines are located and purchased/obtained from seed dealers or growers.

4. All varieties are assigned a number to maintain integrity and anonymity.

5. Trials are set up in with all necessary varieties. Variety arrangement for trial is diagramed.

II. Planting

1. Commercial plantings are located by contacting commercial growers during the planting slot recommended for the variety.

2. A field is located during commercial planting and the necessary rows and area is marked off.

3. Varieties are planted according to a diagram, generally in 100 foot ranges.

4. All varieties are planted in same manner to mimic the planting of the commercial variety as closely as possible.

5. A trial map is drawn diagramming the trial, the trial location in the field and directions to the field.

III. Maintenance

1. All tested varieties are treated identically. Plants are watered, fertilized, and treated to control pests in the same manner as other lettuce plants in the commercial field.

2. Thinning the trial is thinned to separate the plants for optimum growth.

IV. Evaluation

1. Evaluations are done as near to the time of the commercial harvest as possible by knowledgeable Progeny employees.

2. The evaluation is conducted "blindly". The evaluator(s) do not have the key to the trial at the time of evaluation.

3. 24 heads of each variety are evaluated. The frame diameter of 24 random plants are measured to the nearest cm. 24 mature heads of each variety are cut to the cap leaf. The heads are carried to an adequate work station. Each head is weighed to the nearest gram. The core diameter (FIG. 1 no. 3) of each head is measured to the nearest mm. The heads are then sliced into halves, discarding 1 half. The core lengths (FIG. 1 no. 4) are measured to the nearest mm. The head length (FIG. 1 no. 1) is measured to the nearest mm. The head diameter (FIG. 1 no. 2) is measured to the nearest mm. The ideal maturity or harvest date is then estimated based on the solidity of the head, the core length (FIG. 1 no. 4), and any other physiological characteristics present. The leaf color is documented using the Munsell Color Charts for Plant Tissue. From these measurements, an Excel program is used to calculate the averages, the standard deviations and the T-Tests for the compared varieties.

Example 2

Comparative Analysis

Following the procedures of Example 1, Pacer iceberg lettuce was compared to various other varieties. Comparative data was obtained and analyzed for different iceberg lettuce lines. Core length (FIG. 1 no. 4), core diameter (FIG. 1 no. 3), head diameter (FIG. 1 no. 2), head length (FIG. 1 no. 1), average head diameter, frame diameter and head weight as provided in the definitions section above. The data are presented in Table 1.

Table 1 shows trial data comparing Pacer and Desert Queen iceberg lettuce varieties.

TABLE 1

| | Trial map #: PD99007 | | | | Location: TesPicos | | Comparison of Head Characteristics | | Commercial variety: Vanfalll | | Maturity Date: | | Days to Maturity | |
| | Wet Date: ##### | | | | Grower: T&A | | Ranch/Lot: 27-2-1 | | | | Pacer 61 | | | |
| | Date evald: ##### | | | | | | | | | | Desert Queen 60 | | | |
| | Core length (cm) | | Core diam (cm) | | Head diam (cm) | | Head length (cm) | | Avg Head Diameter (cm) | | Avg Head Diam Core Length | | Frame diam (cm) | | Head wt (g) | |
| Sample # | Pacer | Desert Queen | Pacer | Desert Queen | Pacer | Desert Queen | Pacer | Desert Queen | Pacer | Desert Queen | Pacer | Desert Queen | Pacer | Desert Queen | Pacer | Desert Queen |
|---|---|---|---|---|---|---|---|---|---|---|---|---|---|---|---|---|
| 1 | 3.3 | 5.2 | 3.5 | 2.9 | 16.5 | 19.0 | 14.9 | 14.5 | 15.7 | 16.8 | 4.8 | 3.2 | 49 | 45 | 982 | 838 |
| 2 | 4.7 | 5.2 | 3.3 | 2.9 | 16.5 | 18.3 | 15.2 | 16.5 | 15.9 | 17.4 | 3.4 | 3.3 | 49 | 48 | 844 | 972 |
| 3 | 4.5 | 4.8 | 3.6 | 3.0 | 15.0 | 18.8 | 16.1 | 13.3 | 15.6 | 16.1 | 3.5 | 3.3 | 47 | 56 | 682 | 960 |
| 4 | 4.0 | 2.5 | 3.5 | 3.1 | 17.5 | 18.0 | 14.7 | 13.5 | 16.1 | 15.8 | 4.0 | 6.3 | 49 | 49 | 794 | 802 |
| 5 | 3.9 | 4.1 | 3.7 | 3.2 | 16.2 | 18.5 | 13.8 | 15.0 | 15.0 | 16.8 | 3.8 | 6.7 | 48 | 53 | 842 | 822 |
| 6 | 5.4 | 3.3 | 3.2 | 3.3 | 16.7 | 16.5 | 15.3 | 12.5 | 16.0 | 14.5 | 3.0 | 3.5 | 48 | 51 | 718 | 854 |
| 7 | 5.0 | 3.2 | 3.4 | 3.0 | 15.9 | 16.2 | 13.8 | 14.6 | 14.9 | 15.4 | 3.0 | 4.7 | 51 | 46 | 664 | 1018 |
| 8 | 4.2 | 4.5 | 3.7 | 3.4 | 16.7 | 16.3 | 13.2 | 14.3 | 15.0 | 15.3 | 3.6 | 4.8 | 49 | 49 | 1028 | 1046 |
| 9 | 8.0 | 3.5 | 4.0 | 2.5 | 15.7 | 16.7 | 14.3 | 13.6 | 14.9 | 16.0 | 1.9 | 3.6 | 56 | 47 | 894 | 884 |
| 10 | 5.3 | 3.3 | 3.6 | 2.7 | 18.1 | 17.5 | 15.8 | 14.6 | 17.0 | 16.1 | 3.2 | 4.6 | 50 | 48 | 910 | 934 |
| 11 | 6.0 | 3.8 | 3.2 | 2.8 | 16.8 | 15.4 | 14.6 | 12.8 | 15.7 | 14.1 | 2.6 | 4.3 | 45 | 46 | 906 | 940 |
| 12 | 4.0 | 5.0 | 3.5 | 2.9 | 18.5 | 20.2 | 15.2 | 14.3 | 16.9 | 17.3 | 4.2 | 4.5 | 46 | 55 | 802 | 1086 |
| 13 | 5.5 | 4.0 | 3.3 | 2.8 | 14.9 | 15.0 | 13.9 | 15.2 | 14.4 | 15.1 | 2.6 | 3.0 | 52 | 54 | 786 | 936 |
| 14 | 5.2 | 4.5 | 3.4 | 3.0 | 16.0 | 18.2 | 13.7 | 15.0 | 14.9 | 16.6 | 2.9 | 4.2 | 53 | 52 | 806 | 809 |
| 15 | 6.0 | 5.5 | 3.0 | 3.3 | 18.0 | 17.6 | 17.5 | 15.8 | 17.8 | 16.7 | 3.0 | 3.7 | 56 | 50 | 886 | 690 |
| 16 | 4.0 | 3.2 | 3.2 | 3.3 | 16.3 | 17.2 | 14.2 | 14.2 | 15.3 | 15.7 | 3.8 | 2.9 | 50 | 46 | 866 | 504 |
| 17 | 4.3 | 3.7 | 3.3 | 3.4 | 15.7 | 16.8 | 13.8 | 15.4 | 14.8 | 16.1 | 3.4 | 4.4 | 57 | 45 | 852 | 816 |
| 18 | 6.1 | 4.3 | 3.3 | 3.2 | 17.2 | 18.2 | 15.3 | 14.0 | 16.3 | 16.1 | 2.7 | 3.7 | 55 | 48 | 862 | 836 |
| 19 | 4.7 | 4.5 | 3.3 | 3.2 | 17.5 | 17.3 | 14.5 | 13.8 | 16.0 | 15.6 | 3.4 | 3.5 | 49 | 44 | 936 | 824 |
| 20 | 6.2 | 5.0 | 3.7 | 3.1 | 17.2 | 18.2 | 15.0 | 12.9 | 16.1 | 15.6 | 2.6 | 3.1 | 52 | 45 | 894 | 760 |
| 21 | 4.8 | 4.4 | 3.6 | 2.5 | 18.5 | 19.1 | 15.7 | 15.1 | 17.1 | 17.1 | 3.6 | 3.9 | 47 | 50 | 790 | 914 |
| 22 | 4.5 | 4.0 | 3.1 | 3.0 | 16.8 | 16.2 | 14.8 | 14.5 | 15.8 | 15.4 | 3.5 | 3.8 | 46 | 48 | 1012 | 936 |
| 23 | 5.2 | 6.5 | 3.6 | 3.5 | 20.0 | 17.3 | 15.2 | 14.0 | 17.6 | 15.7 | 3.4 | 2.4 | 49 | 49 | 1000 | 706 |
| 24 | 5.0 | 5.0 | 3.9 | 2.5 | 18.6 | 17.2 | 16.2 | 14.0 | 17.4 | 15.9 | 3.5 | 3.1 | 48 | 47 | 1002 | 762 |
| Average | 5.0 | 4.3 | 3.5 | 3.0 | 17.0 | 17.6 | 14.9 | 14.3 | 15.9 | 15.9 | 3.3 | 3.9 | 50.0 | 48.8 | 864.9 | 860.4 |
| Stan dev | 1.00387 | 0.9059785 | 0.2500725 | 0.2802367 | 1.2279 | 1.2356715 | 0.988 | 0.9577676 | 0.9659 | 0.81849101 | 0.61796851 | 1.0028491 | 3.3425 | 3.30979 | 100.16 | 12696963 |
| T test | 1.47E-02 | | 5.48E-07 | | 9.39E-02 | | 6.00E-02 | | 8.98E-01 | | 1.05E-02 | | 1.99E-01 | | 8.91E-01 | |

| Variety | Pacer | Desert Queen |
|---|---|---|
| Color | 5gy5/8 | 5gy6/6 |
| Tip burn | 8/24 | 21/24 |
| Tip severity | 1 | 2.5 |
| Solidity | 5 | 4.3 |

Solidity
1 = very loose
5 = Very solid
Tip Severity
1 = light
5 = severe

Pacer is a distinct variety of iceberg lettuce due to its type and adaptability. Pacer is a vanguard type variety that is a sure heading and large framed with excellent tolerance to heat. Pacer performs excellent during earliest fall plantings in the lettuce production region of Huron Calif., typically limited to empire type varieties.

Pacer is very distinct from its seed bearing parent Desert Queen. Where as Desert Queen is a large heading empire type, Pacer has a much less frilled leaf margin and is a distinct Vanguard type of iceberg lettuce. The varieties are similar in size and color, but Pacer also demonstrates improved texture, and improved heading characteristics typical of vanguard type varieties. A vanguard type variety is preferred over the older empire types, due to their improved texture, head shape, growing habit, and shelf life.

Pacer most closely resembles the commercial variety Raider. Pacer is distinguished from the variety Raider by seed color, heat resistance and size. Pacer is white seeded and has increased heat tolerance as indicated by measured core lengths and planting slots. Recommended planting dates for Pacer during the fall plantings in Huron begin on August 8$^{th}$, Raider is planted nearly 2 weeks later, beginning on August 20$^{th}$. Pacer demonstrates a more compact head and shorter core length as indicated from the trial results.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

We claim:

1. A *Lactuca sativa* seed designated as Pacer having ATCC Accession Number PTA-4010.

2. A *Lactuca sativa* plant produced by growing the seed of claim 1.

3. A *Lactuca sativa* plant having all of the physiological and morphological characteristics of the *Lactuca sativa* of claim 2.

4. Pollen of the plant of claim 2.

5. An ovule of the plant of claim 2.

6. A tissue culture of the plant of claim 2.

7. A method of selecting *Lactuca sativa*, comprising a) growing more than one plant from the seed of claim 1 b) selecting a progeny plant from step a) wherein said progeny plant is phenotypically distinguishable from the parent plant.

8. A method of making an $F_1$ hybrid lettuce plant consisting of crossing Pacer as a first lettuce parent plant with a second lettuce parent plant, wherein said first lettuce plant is grown from the seed of claim 1, harvesting the resultant $F_1$ hybrid seed, and growing an $F_1$ hybrid seed into an $F_1$ hybrid lettuce plant.

* * * * *